United States Patent
Ashman

(10) Patent No.: US 6,722,884 B2
(45) Date of Patent: Apr. 20, 2004

(54) METHOD AND APPARATUS FOR PERFORMING RIDGE PRESERVATION AND IMPLANT TREATMENT

(76) Inventor: Arthur Ashman, 153 Bayberry La., Westport, CT (US) 06880

(*) Notice: Subject to any disclaimer, the term of this patent is extended or adjusted under 35 U.S.C. 154(b) by 42 days.

(21) Appl. No.: 09/970,187

(22) Filed: Oct. 2, 2001

(65) Prior Publication Data

US 2002/0009692 A1 Jan. 24, 2002

Related U.S. Application Data

(62) Division of application No. 09/421,599, filed on Oct. 20, 1999, now Pat. No. 6,325,627.

(51) Int. Cl.⁷ ............................................. A61C 8/00
(52) U.S. Cl. ...................................... 433/173; 433/215
(58) Field of Search .............................. 433/172, 173, 433/174, 175, 201.1, 215

(56) References Cited

U.S. PATENT DOCUMENTS

| | | |
|---|---|---|
| 4,051,598 A | 10/1977 | Sneer |
| 4,244,689 A | 1/1981 | Ashman ................... 433/175 |
| 4,535,485 A | 8/1985 | Ashman et al. |
| 4,536,158 A | 8/1985 | Bruins et al. ............ 433/201.1 |
| 4,547,327 A | 10/1985 | Bruins et al. |
| 4,547,390 A | 10/1985 | Ashman et al. |
| 4,728,570 A | 3/1988 | Ashman et al. |
| 4,738,623 A | 4/1988 | Driskell ................... 433/173 |
| 4,872,840 A | 10/1989 | Bori ......................... 433/173 |
| 5,246,370 A | 9/1993 | Coatoam ................. 433/173 |
| 5,372,503 A | 12/1994 | Elia ......................... 433/215 |
| 5,397,235 A | 3/1995 | Elia ......................... 433/173 |
| 5,685,716 A | 11/1997 | Linkow ................... 433/173 |
| 5,915,967 A | 6/1999 | Clokie ..................... 433/173 |
| 6,132,214 A | 10/2000 | Suhonen et al. ........ 433/201.1 |

OTHER PUBLICATIONS

A. Norman Cranin, et al., Abstract:"The Use of a Particulate, Microporous, Calcified Copolymer as a Ridge Maintenance Device in Dogs," Joural of Veterinary Dentistry, 12(2):53–58, (Jun. 1995).

U.S. patent application Ser. No. 09/248,079, Ashman et al.

Primary Examiner—Cary E. O'Connor
(74) Attorney, Agent, or Firm—Darby & Darby

(57) ABSTRACT

A method for preserving the alveolar ridge surrounding a presently extracted root socket by backfilling the socket with bone graft material and installing an implant in the root socket area either immediately before backfilling or after backfilling and a delay in which new bone is allowed to grow into the bone graft material. In one embodiment, the dental implant is installed apically into the root socket immediately following root extraction. The open area of the root socket surrounding the implant is then backfilled with bone graft material immediately after implant placement. The implant is preferably a threaded implant (but it can be a cylinder-type) which is placed approximately three to six millimeters apically to said root socket. The bone graft material comprises synthetic bone alloplast such as Bioplant® HTR® and is hydrated using the patient's own blood obtained from the patient's bleeding extraction socket after penetration but prior to insertion of the bone graft material and the implant into said root socket. As an alternate embodiment, the presently extracted root socket is filled with bone graft material and primary or non-primary closure of the extraction site is performed. Bone-growth is promoted in the root socket by the bone graft material for 2–12 months. Then, after sufficient bone growth has been promoted, an implant is installed in the extraction site area in the normal manner.

18 Claims, 3 Drawing Sheets

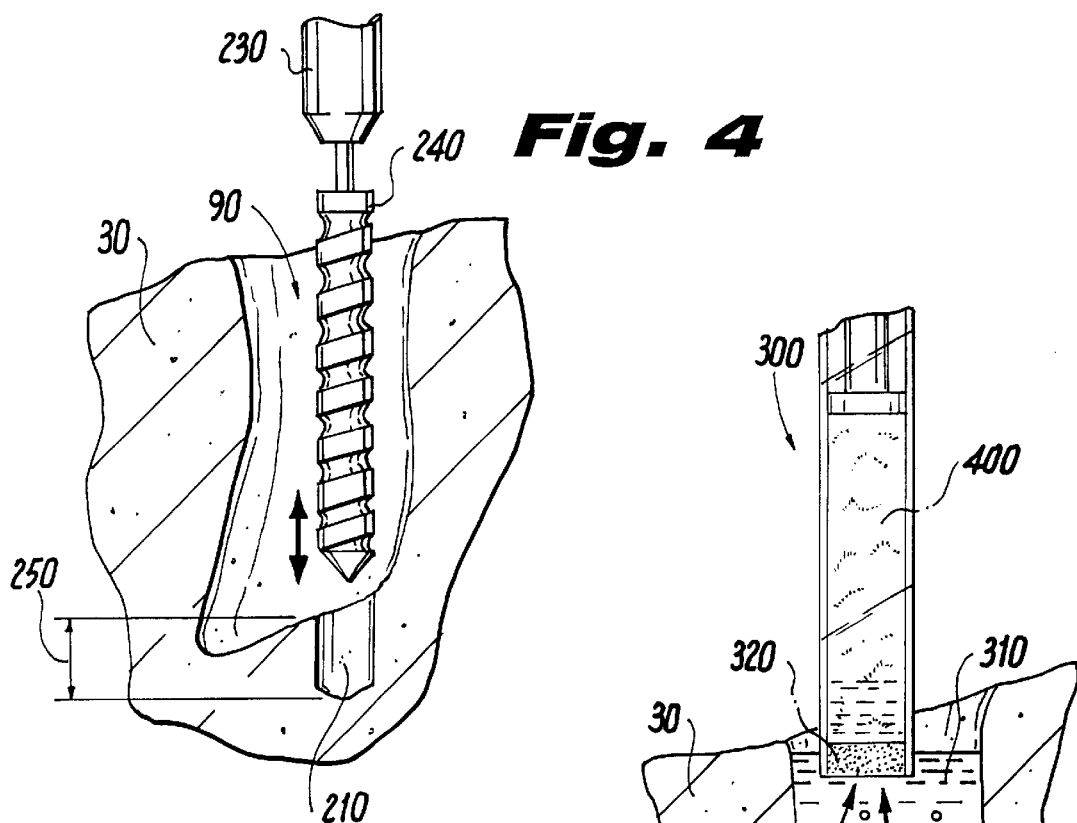
Fig. 4
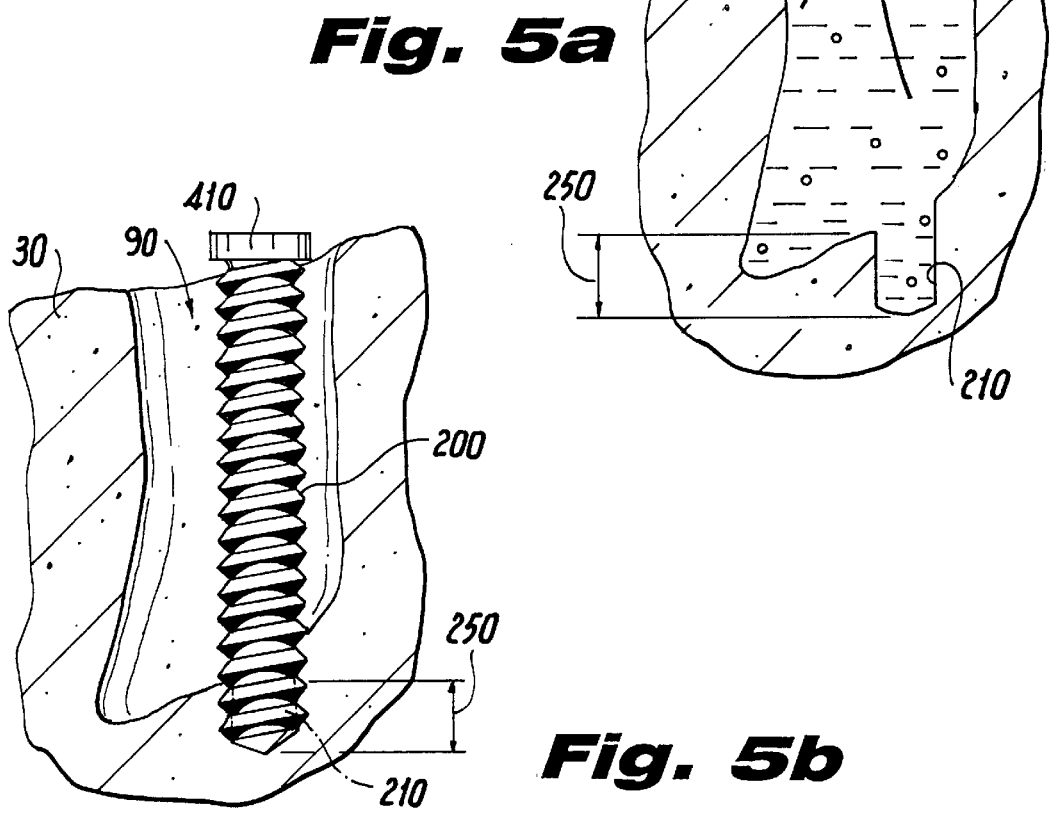
Fig. 5a
Fig. 5b

METHOD AND APPARATUS FOR PERFORMING RIDGE PRESERVATION AND IMPLANT TREATMENT

This is a divisional of application Ser. No. 09/421,599, filed on Oct. 20, 1999, now U.S. Pat. No. 6,325,627. Each prior application is incorporated herein by reference in its entirety.

FIELD OF THE INVENTION

The present invention relates to dental procedures in general and, more particularly, to a method and apparatus for installing bone graft material and an implant in a tooth root extraction socket following a root extraction.

BACKGROUND OF THE INVENTION

According to the National Survey on Oral Health conducted by the National Institute of Dental Research, approximately 42 percent of Americans over 65 years of age and four percent of those 35 to 64 are totally edentulous. Moreover, those over 65 years old who still have some of their teeth have lost an average of 12 of their 28 teeth, and persons aged 55 to 64 have lost an average of nine of their 28 teeth.

When an extracted or otherwise missing tooth is not replaced, atrophy of the jaw bone occurs over time. Consequently, individuals who have been partially or fully edentulous for an extended period of time are left with an atrophic alveolar ridge that can not securely support a full or partial denture or support the placement of a dental implant. Furthermore, the edentulous individual faces a continuing deterioration of aesthetics and a compromised ability to chew leaving the quality of the individual's oral life in an unfortunate state.

FIGS. 1 through 3 illustrate the deteriorating effect of tooth extraction on the alveolar ridge. Turning to FIG. 1, a tooth of a patient, comprised of a crown 10 and root 20, are shown seated in the alveolar (or jaw) bone 30. The buccal and lingual portion of the alveolar bone is surrounded by a layer of tissue known as the gingiva or gum 40. The crown 10 and root 20 are supported by the alveolar ridge or jaw bone 30 and the gingiva 40 which, in the ideal case, is adjacent to the tooth at a level gum line 50 over the underlying bone. Crown height line 60 is shown. When such a tooth or series of teeth become infected or otherwise dentally compromised such that the extraction of the crown 10 and root 20 are required, the root 20 is removed from the alveolar bone 30 by separating the surface of the root 20 from the periodontal membrane 70.

FIG. 2 represents the portion of the alveolar bone 30 shortly after extraction of the crown 10 and root 20. As is shown, the alveolar bleeding clots, such that bleeding ceases and a root extraction socket 90 remains in the alveolar bone 30 in the shape of the extracted root 20.

The buccal and lingual portions of the alveolar bone 30 are composed of bone which has a unique characteristic, i.e., being capable of absorbing the shocks caused by the stress movement of teeth during speech, eating, etc. The removal of a tooth and the resulting absence of frequent use pressure in the area causes the alveolar bone 30 to shrink (i.e., be resorbed) in that area where pressure is no longer applied (the extraction site) with the subsequent loss of 40 to 60 percent (in a 2 to 4 year time) of the alveolar ridge's former height measured at the gum line 50 (i.e., "disuse atrophy"). FIG. 3 shows an extraction site with various degrees of loss of buccal and crestal alveolar bone 30 two years after the extraction of the tooth represented in FIG. 1. The jaw bone continues to atrophy at a bone loss rate of one-half to one percent per year until death of the patient.

Bone graft substitute material has been used to immediately fill a root extraction socket 90 at an extraction site after a root 20 extraction in order to promote bone growth and to avoid the expected bone atrophy, i.e., Ridge Preservation. Bone growth is promoted via the bone graft material's intermixing with the patient's own marrow blood which seeps through the root extraction socket 90. After an appropriate time period to allow alveolar bone regeneration (approximately 12 to 18 months) dense lamina bone forms in the extraction socket area. The patient may then be considered for a denture prosthesis.

The method of applying bone graft material to a newly extracted root site is known. What is desired is a method for installing an implant in a root extraction socket and backfilling the socket area immediately after extraction, i.e., immediate post-extraction implant installation. What is alternately desired is a method for backfilling a root extraction socket with bone graft material immediately after extraction and then delaying installation of an implant in the root extraction socket until bone graft material has promoted sufficient bone growth in the root extraction socket, i.e., delayed post-extraction implant installation.

SUMMARY OF THE INVENTION

It is accordingly an object of the present invention to provide a method and apparatus for immediate post-extraction installation of an implant by (a) immediately installing an implant in a root extraction socket following root extraction and (b) filling the remaining space in the socket with bone graft material to encourage new bone growth in the extraction site and subsequent osseointegration of the implant.

According to an aspect of the invention, a method and apparatus for preserving the alveolar ridge around a newly extracted root socket and providing an implant comprises the steps of installing a dental implant apically 3 to 6 mm to the root extraction socket, filling the remaining open area of the root extraction socket with bone graft material and retaining the bone graft material during initial healing of the bone and gingiva with a restraint such as sutures, or a collagen or a surgical foil dressing.

It is a further object of the present invention to provide a method and apparatus for delayed post-extraction installation of an implant by filling the root extraction socket with bone graft material immediately after root extraction and, after sufficient new bone growth has been promoted by the bone graft material in the root extraction socket, installing an implant in the new bone growth utilizing known methods and apparatus for installing an implant in a normal, non-atrophied jaw bone.

BRIEF DESCRIPTION OF THE DRAWINGS

Other objects and features of the present invention will be described hereinafter in detail by way of certain preferred embodiments with reference to the accompanying drawings, in which:

FIG. 4 is a cross-sectional view of a hole drilled apically to a root extraction socket to accommodate implant placement;

FIG. 5a is a cross-sectional view of blood from the marrow bleeding of the alveolar bone of the root extraction socket being drawn into a syringe filled with bone graft material;

FIG. 5b is a cross-sectional view of an implant placed apically to the root extraction socket into the hole illustrated in FIG. 4;

DETAILED DESCRIPTION OF THE PRESENT INVENTION

1. Immediate Post-Extraction Implant

Figure 1:
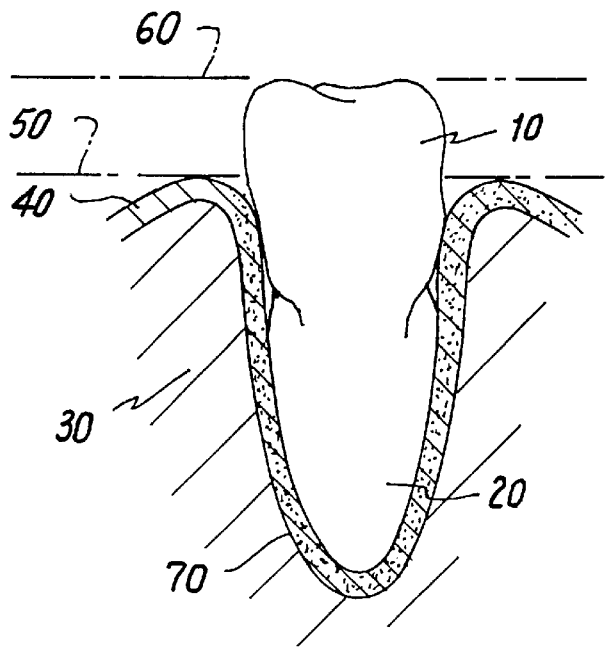
FIG. 1 is a cross-sectional view of a tooth crown and root prior to extraction from the alveolar bone.
Figure 2:
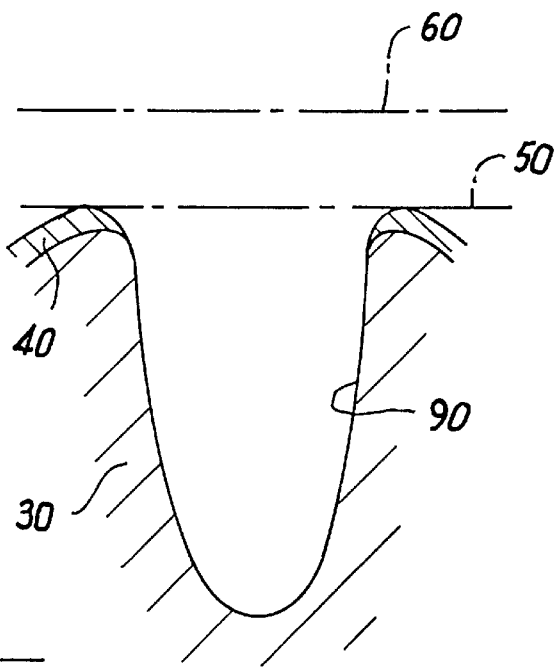
FIG. 2 is a cross sectional view of the alveolar ridge following the extraction of the root illustrated in FIG. 1.
Figure 3:
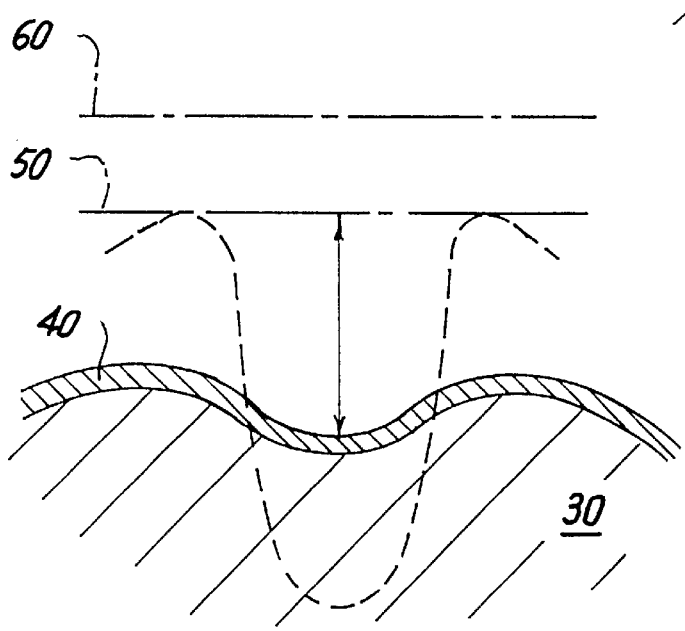
FIG. 3 is a cross-sectional view an atrophied alveolar ridge two to four years following the root extraction illustrated in FIG. 2.

With reference to FIGS. 1 and 2 the dental surgeon commences the procedure of replacing a deteriorated, hopeless tooth with an artificial tooth by extracting the appropriate root 20 or roots of the affected tooth or teeth in the normal manner, e.g., full thickness mucoperiosteal flaps with bilateral vertical released incisions if necessary. The procedure may be utilized on teeth and/or roots of either the mandible or the maxilla. The extraction of the root 20 will cause the alveolar bone marrow to bleed through a resulting root extraction socket 90. The dental surgeon then performs vigorous debridment and suction of the root extraction socket 90 to remove all infectious and periodontal membrane 70 remnance, and to stimulate marrow bleeding from the socket. A small layer of dead or infected socket bone may also be debrided with a suitable rotary bur (1 to 3 mm).

As shown in FIG. 4, the dental surgeon preferably thereafter, in accordance with methods known in the art, utilizes a dental handpiece 230 and a bone drill 240 to drill a hole 210 3 to 6 mm (depth indicated by line axis 250) apically to the root extraction socket 90. The hole 210 promotes marrow bleeding in the root extraction socket 90 and serves as an extension of the root extraction socket 90 into which a dental implant is secured as explained below.

Following drilling of the hole 210 as in FIG. 4, the dental surgeon hydrates any one of many bone graft materials at the area surrounding the root extraction socket 90. Although many bone graft materials, such as Bioglass®, Osteograf®, Oestrogen®, etc. may be utilized, Bioplant®, Inc.'s Hard Tissue Replacement or HTR®, which is a synthetic bone alloplast, is preferably used. As will be explained, using HTR® to fill the area surrounding the implant promotes bone growth in the socket area whether used with or without a barrier membrane (e.g., a resorbable or non-resorbable membrane) thereby maintaining the height and width of the alveolar ridge and preventing the natural process of atrophy which normally follows root extraction, i.e, "Ridge Preservation". The dental surgeon may additionally mix the graft material with the patient's own bone (e.g., from the hip bone, or from other areas of the jawbone, e.g., chin) in order to promote faster and more effective growth of bone in the alveolar ridge through the use of bone precursor cells.

Although the HTR® can be wetted (hydrated) with liquid antibiotic, liquid recombinant bone-inducer factors or sterile saline solution, blood from the surgical area of the patient's alveolar marrow is preferably used to wet the HTR® or other graft material utilized. Accordingly, as shown in FIG. 5a, the dental surgeon uses a filter-tipped straight or curved syringe 300, such as HTR®-24 Straight Syringe, Item #H216102 or HTR®-24 Curved Syringe, Item #H216112 available from Bioplant®, Inc. of 20 North Main Street, Norwalk, Conn. 06854, filled with 750 micron diameter HTR® to absorb blood 310 from the bleeding root extraction socket 90 and the hole 210. The dental surgeon thereafter allows the blood wetted HTR® 400 to congeal for 2 to 4 minutes at the conclusion of which time he removes the filter tip 320 from the syringe 300. U.S. patent application Ser. No. 08/831,941 describing the syringe 300, and special tip 320, and a method for using the same is hereby incorporated in its entirety by reference.

As illustrated in FIG.. 5b, during hydration of the graft material, the dental surgeon inserts an implant 200, preferably a threaded titanium screw, into the hole 210 apical to the root extraction socket 90. Alternately, a HA coated screw or cylinder or non-HA coated cylinder implant may be used. The installation of the implant 200 is done in the normal manner and preferably utilizes torque reduction rotary instruments at 500 r.p.m. using copious irrigation with chilled sterile physiological saline solution. Lower speeds may be used without irrigation. Hand instruments may also be used for insertion. By installing the implant 200 into the alveolar bone 30 at 210, the implant 90 is firmly anchored to the alveolar bone 30 rendering the implant sufficiently immobile. If the implant is not sufficiently immobile (i.e., it is loose) following implant installation, the implant 200 is removed and replaced with a larger implant. The dental surgeon thereafter places a healing cap 410 (i.e., an abutment) onto the head of the implant 200 using a hand instrument with a rachet with no irrigation. The dental surgeon may utilize any of the screw implants of appropriate composition, length and width known in the art, depending upon the size and dimension of the extracted tooth's socket and the state of the alveolar ridge.

Figure 6:
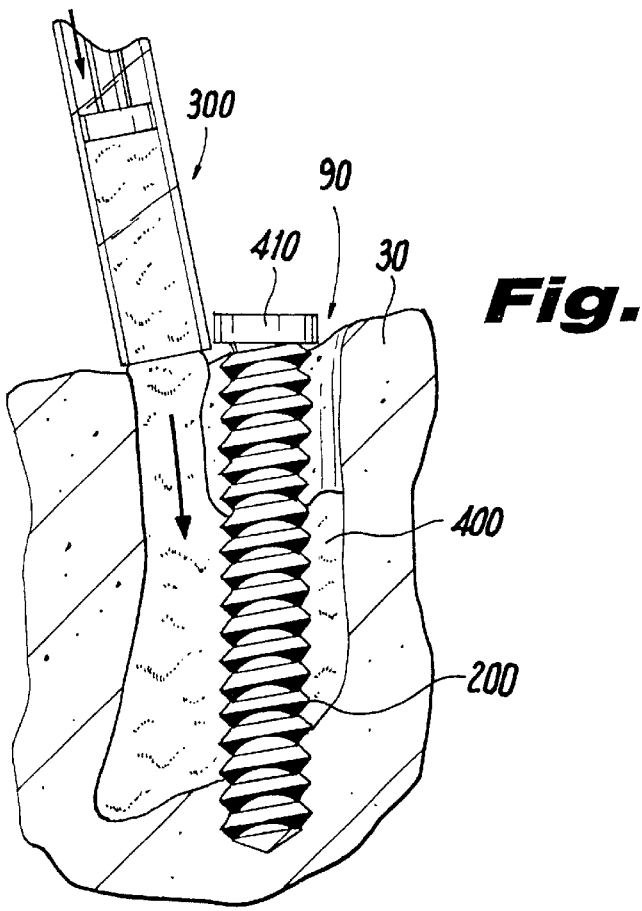
FIG. 6 is a cross-sectional view of the root extraction socket illustrated in FIG. 4 with an installed implant being filled with previously blood-wetted bone graft material.

As illustrated in FIG. 6, the dental surgeon then expels the wetted HTR® 400 into and around the root extraction socket 90. The dental surgeon expels an amount of wetted HTR® 400 sufficient to fill the root extraction socket 90 up to the height of the alveolar ridge surrounding the bone voids around the dental implant 200. The wetted HTR® 400 is of a paste-like, moldable form which lends itself to being shaped. The dental surgeon compacts the wetted HTR® 400 up to and surrounding the implant neck (e.g., "backfilling"), but does not cover the healing cap 410. Firm but minimal pressure is used in packing the HTR® 400, such that the implant 200 does not move as a result of the HTR® packing. If the implant 200 is loose enough in the root extraction socket 90 to move at this point, it should be removed and replaced with a larger sized implant because graft material will not help to tighten a loose implant. The wetted HTR® 400 adheres immediately to the alveolar bone 30 and the implant 200, causing the root extraction socket 90 bleeding to clot.

After the remaining void of the root extraction socket 90 is filled with wetted HTR® 400, the dental surgeon accomplishes primary closure using any of the varying methods known in the art. The dental surgeon may utilize two vertical relief incisions and undermining using silk sutures for soft tissue closure. Alternately, the dental surgeon may use a surgical foil (e.g., Biofoil®) or a collagen dressing or any other protective device to hold the bone graft material in place and to protect the bone graft material from the patient's tongue or food displacement. When HTR® is used as the bone graft material, a dense fibrous barrier "membrane" is naturally formed by the HTR® under the gingiva flap and, accordingly, it is possible that no further barrier membrane or other bone graft holding material may be necessary.

As is known in the art, when accomplishing primary closure the dental surgeon may leave the healing cap 410 exposed (one-stage implant) or he may alternately cover the healing cap via soft tissue closure (two-stage implant). As will be explained and as is known in the art, the two-stage implant procedure requires that an additional surgical procedure be performed at a later point after implantation whereas use of the one-stage implant procedure does not require that an additional surgical procedure be performed. The dental surgeon is free to utilize either the one-stage or two-stage implant procedure considering such factors as, e.g., the possibility of infection and/or other post-operative considerations.

The dental surgeon may thereafter prescribe systemic antibiotics and analgesics for seven to ten days as is known in the art. If resorbable sutures were used to promote healing, removal of the sutures is not thereafter necessary. The dental surgeon then carefully cleans the area. The patient should keep the area clean during this time preferably using a germ reducing (e.g., Peridex rinse).

Figure 7:
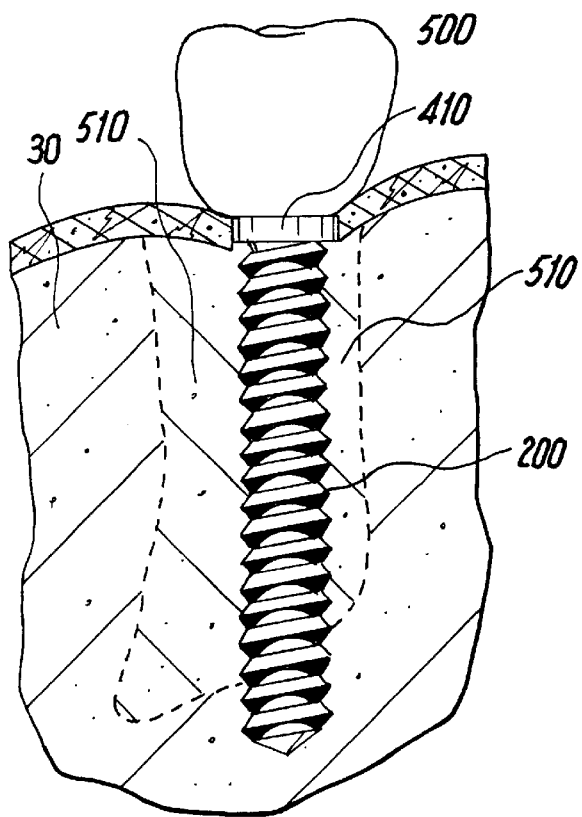
FIG. 7 is a cross-sectional view of an implant secured (osseointegrated) in newly regenerated lamina bone capable of supporting a prosthetic crown and implant.

With reference to FIG. 7, approximately 4 to 10 months after implant installation (depending upon the patient), the dental surgeon exposes the healing cap 410 of the implant 200 using gum surgery or punch techniques where the two-stage implant procedure was utilized. As previously explained, if a one-stage implant procedure was utilized, gum surgery and/or punch techniques are not necessary to expose the healing cap 410 because the healing cap 410 will already be exposed.

In either case, as shown in FIG. 7, the dental surgeon thereafter performs prosthetic procedures which may include the mounting of a prosthetic crown 500 on the implant 200 in the normal manner.

Over the course of the 4 to 10 month post-implant period, the HTR® will have promoted bone growth in the area of the root extraction socket 30 by osteoconduction such that the implant 200 will have been osseointegrated in an HTR®-bone complex 510. By the addition of bone growth factors to a graft material's surface (e.g. BMP, OP-1, angiogenic factors, plasma factors, synthetic peptides, etc . . . ), HTR® is made osteoinductive. Osteoinductivity reduces the bone healing rate, and subsequent bone regeneration is considerably faster (e.g. it may take weeks instead of months or years). Furthermore by having immediately backfilled the extraction socket 30 with HTR® or other graft bone substitute materials months earlier, the normal resorption rate (40 to 60% in 2 to 4 years) of the jaw bone associated with tooth extractions is avoided. Also, because the implant was inserted immediately after the extraction of the root, an additional surgical procedure, namely the implantation, is avoided. The patient is given an immediate implant directly after losing a tooth.

The methods described above may be modified to support other prosthetic structures such as a superstructure. When multiple, contiguous, and damaged or otherwise unhealthy roots are extracted, the above procedure is used to install an implant into each socket and then backfill each root extraction socket with bone graft material in accordance with the methods described above.

Thereafter, in accordance with the above-described method, approximately 4 to 10 months after the multiple implants are installed, the dental surgeon exposes the healing caps of the implants using gum surgery or punch techniques where the two-stage implant procedure was utilized. If a one-stage procedure was utilized, a secondary surgical technique is not necessary. In either case, the dental surgeon thereafter performs prosthetic procedures which may include the mounting of superstructure on the implants in the normal manner.

2. Delayed Post-Extraction Implant

In addition to the above-described method and apparatus for immediately installing an implant in a root extraction socket, i.e, immediate post-extraction installation of an implant, an alternate method for post-extraction installation of an implant (i.e., delayed post-extraction installation of an implant) includes: (a) filling a root extraction socket 90 with bone graft material and (b) delaying implantation of an implant in the root extraction socket until a later time, i.e., after the bone graft material has promoted sufficient new bone growth in the root extraction socket.

In accordance with the above-mentioned delayed post-extraction implant installation method, the dental surgeon proceeds as previously described with respect to the immediate post-extraction implant installation implant method as shown in FIG. 2, i.e., the dental surgeon extracts the damaged or decayed root 20 in the normal manner.

Rather than proceeding to the step of drilling the hole 210 apically to the root extraction socket 90 as illustrated in FIG. 4, however, the dental surgeon instead proceeds to the step of hydrating the bone graft material, e.g., the HTR® 400, as shown in FIG. 5a. The dental surgeon utilizes blood caused by the root extraction as the hydrating agent for the HTR®.

As with the immediate post-extraction implant installation procedure, the dental surgeon allows the blood-wetted HTR® to congeal for 2 to 4 minutes in the syringe 300 and then expels the wetted HTR® 400 into the root extraction socket 90 as shown in FIG. 6 (without implant 200). As previously described, the HTR® may be mixed with the patient's own bone.

The dental surgeon then compacts the wetted HTR® up to the gum line 50 and accomplishes primary closure using any of the methods known in the art. Alternately the dental surgeon may use a surgical foil or collagen or other dressing to hold the graft material in place (as a protectant) either with or without primary closure (suturing).

The dental surgeon may thereafter prescribe systemic antibiotics and analgesics for seven to ten days as is known in the art. If resorbable sutures were used to promote healing, removal of the sutures is not thereafter necessary. The dental surgeon then carefully cleans the area. The patient should keep the area clean during this time preferably using a germ reducing rinse, e.g., "Peridex" rinse.

Thereafter, depending upon the patient, the dental surgeon returns to the extraction site 2 to 12 months after extraction and installs an implant in the HTR® generated bone complex. From the time of the implantation, the HTR® will have promoted sufficient bone growth in the root extraction socket 90 so as to allow the secure installation of an implant using known methods for installing an implant in a normal, non-atrophied jaw bone. Any of the implants and methods for installing an implant in a normal non-atrophied jaw bone that are known in the art may be used.

The amount of time the dental surgeon waits prior to proceeding with implant installation is dependent upon the patient and, more particularly, upon the bone growth rate of the HTR®-bone complex. The longer the HTR® is permitted to remain in the root extraction socket prior to implant installation, the greater the amount of dense bone that will have been created by the HTR®-bone complex and, accordingly, the greater will be the density of the bone created in the root extraction socket. Greater bone density provides for a more secure implant.

As previously stated, an implant may be installed in the root extraction socket as early as 2–6 months after the HTR® is inserted into the root extraction socket. The bone that will have been formed at this point by the HTR®-bone complex will be immature bone, i.e., osteoid. If the dental surgeon installs the implant in osteoid, the dental surgeon waits approximately 6 months before returning to the site to install a crown 500 on the implant as in FIG. 7 in the manner known in the art. However, if the dental surgeon waits a longer period of time before installing the implant, e.g., more than 6 months, the bone into which the implant is installed will be more mature and, therefore, denser. Accordingly, the dental surgeon may wait a shorter period of time, e.g., 3 months, before placing a crown 500 on the implant in the manner known in the art.

The above described delayed post-extraction implant installation method may be modified to support other prosthetic structures such as a superstructure. When multiple, contiguous, and damaged or otherwise unhealthy roots are extracted, the delayed post-extraction implant method is used to backfill each of the multiple root extraction sockets with bone graft material and thereafter, e.g., 2 to 12 months later, an implant is installed in each of the root extraction sockets having HTR®-bone generated complex therein in accordance with the above-described delayed post-extraction implant installation method for a single root extraction socket.

While the present invention has been particularly shown and described with reference to the preferred embodiment thereof, it will be understood by those skilled in the art that various changes in form and details may be made therein without departing from the spirit and scope of the invention.

What is claimed is:

1. A method for preserving a patient's alveolar ridge surrounding one, or a plurality of, a presently extracted root socket comprising the steps of:
    filling the open area of said root socket with bone graft material;
    installing an implant in said filled area after sufficient bone growth has been promoted in said filled area.
2. The method of claim 1, including the additional step of covering the opening of said root socket with a retaining barrier following the step of filling the open area.
3. The method of claim 2, wherein said retaining barrier comprises a barrier membrane.
4. The method of claim 2, wherein said retaining barrier comprises a surgical foil.
5. The method of claim 2, wherein said retaining barrier comprises a collagen dressing.
6. The method of claim 1, wherein said bone graft material is a bone substitute.
7. The method of claim 6, wherein said bone substitute is a synthetic bone alloplast.
8. The method of claim 1, wherein said bone graft material is wetted with said patient's blood, wherein said blood used to wet said bone graft material is obtained from the patient's bleeding root socket.
9. The method of claim 8, wherein said blood from the patient's root socket is drawn by a syringe.
10. The method of claim 9, wherein said syringe is prepackaged with bone graft material.
11. The method of claim 9, wherein the wetting of said bone graft material by the patient's blood occurs inside the syringe.
12. The method as in claim 1, wherein said installing step occurs in approximately 2 to 12 months after said filling step.
13. The method of claim 1, including the additional step of placing a prosthetic tooth on one or more of said implants.
14. The method of claim 13, wherein said placing step occurs in approximately 3 to 6 months after said installing step.
15. The method of claim 13, wherein none of said bone graft material is sintered.
16. The method as in claim 1, wherein said installing step includes forming an opening in said filled area and installing said implant in said opening, said opening being configured so that said implant at least nearly completely occupies said opening.
17. The method of claim 1, wherein said bone graft material is comprised of particles having a diameter of about 750 microns.
18. A method for preserving a patient's alveolar ridge surrounding one, or a plurality of, a presently extracted root socket comprising the steps of:
    filling the open area of said root socket with bone graft material, wherein at least part of said bone graft material is not sintered; and
    installing an implant in said filled area after sufficient bone growth has been promoted in said filled area.

* * * * *

UNITED STATES PATENT AND TRADEMARK OFFICE
CERTIFICATE OF CORRECTION

PATENT NO. : 6,722,884 B2
DATED : April 20, 2004
INVENTOR(S) : Arthur Ashman

It is certified that error appears in the above-identified patent and that said Letters Patent is hereby corrected as shown below:

Title page,
Item [*] Notice, please insert -- This Patent is subject to a Terminal Disclaimer --

Signed and Sealed this

Twenty-seventh Day of July, 2004

JON W. DUDAS
*Acting Director of the United States Patent and Trademark Office*